(12) United States Patent
Ying

(10) Patent No.: US 10,513,610 B1
(45) Date of Patent: Dec. 24, 2019

(54) SULFONATED 4,7-DICHLORORHODAMINE DYES AND THEIR APPLICATION

(71) Applicant: Laiqiang Ying, North Potomac, MD (US)

(72) Inventor: Laiqiang Ying, North Potomac, MD (US)

(73) Assignee: Laiqiang Ying, North Potomac, MD (US)

( * ) Notice: Subject to any disclaimer, the term of this patent is extended or adjusted under 35 U.S.C. 154(b) by 0 days.

(21) Appl. No.: 16/105,713

(22) Filed: Aug. 20, 2018

(51) Int. Cl.
  *C09B 11/24* (2006.01)
  *C07H 19/20* (2006.01)
  *G01N 33/58* (2006.01)

(52) U.S. Cl.
  CPC .............. *C09B 11/24* (2013.01); *C07H 19/20* (2013.01); *G01N 33/582* (2013.01)

(58) Field of Classification Search
  CPC ....... C09B 11/24; C07H 19/20; G01N 33/582
  See application file for complete search history.

(56) References Cited

U.S. PATENT DOCUMENTS 5,800,996 A * 9/1998 Lee .................. C07H 21/00
435/6.12

* cited by examiner

*Primary Examiner* — Timothy R Rozof

(57) ABSTRACT

The invention describes the preparation and use of sulfonated 4,7-dichlororhodamine dyes having the structure:

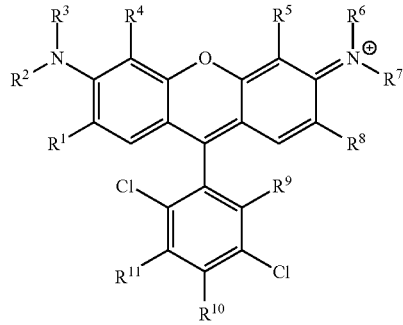

Wherein $R^1$, $R^4$, $R^5$ and $R^8$ are independently hydrogen, —$SO_3Y$ where Y is H or a counterion, $C_1$-$C_6$ alkyl, or $C_1$-$C_6$ alkoxy, where each alkyl or alkoxy is optionally further substituted by a carboxylic acid, a salt of carboxylic acid, or a carboxylic acid ester of a $C_1$-$C_6$ alcohol; $R^2$ and $R^3$ are independently hydrogen, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl; or $R^2$ in combination with $R^1$, or $R^3$ in combination with $R^4$, or both, form a 5- or 6-membered ring that is saturated or unsaturated, and is optionally substituted by one or more $C_1$-$C_6$ alkyls, or —$CH_2SO_3Y$ moieties; $R^6$ and $R^7$ are independently hydrogen, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl; or $R^6$ in combination with $R^5$, or $R^7$ in combination with $R^8$, or both, form a 5- or 6-membered ring that is saturated or unsaturated, and is optionally substituted by one or more $C_1$-$C_6$ alkyls, or —$CH_2SO_3Y$ moieties; $R^9$ is carboxylate or sulfonate; $R^{10}$ and $R^{11}$ are independently hydrogen, Cl, or $R_x$, where $R_x$ is a reactive group. In one aspect, the invention includes reagents labeled with the sulfonated 4,7-dichlororhodamine dye compounds, including an amino acid, peptide, protein, antibody, polysaccharide, nucleotide, nucleic acid, hapten, drug, lipid, polymer, cell, bacterium, yeast, or virus. In an additional aspect, the invention includes methods utilizing such dye compounds and reagents including protein labeling, dideoxy polynucleotide sequencing and fragment analysis methods.

12 Claims, 4 Drawing Sheets

SULFONATED 4,7-DICHLORORHODAMINE DYES AND THEIR APPLICATION

CROSS-REFERENCE TO RELATED APPLICATIONS

This application claims the benefit of U.S. Provisional Application No. 62/547,336, filed Aug. 18, 2017, which application is incorporated herein by reference in its entirety.

BACKGROUND

Fluorescent dyes have been widely used in biological research and clinical diagnosis in which a high sensitive fluorescence detection is desirable. Compared to radioactive detection, fluorescent dyes are less expensive and less toxic. In particular, a diversity of fluorescence dyes with different emission wavelengths has been successfully used for multiplex detection in parallel, such as immunoassay, PCR reaction, SNP, and DNA sequencing. The fluorescent dyes with fluorescence emission maxium in the near infrared region have also been used for in vivo imaging. In addition, the fluorescent dyes have important applications in high-throughput screening.

Despite the diverse applications of fluorescent dyes, the conventional dyes have some limitations in biological applications. First, the conventional dyes are easily prone to self-quenching by dimer formation, a phenomenon known to diminish the effective brightness of the dyes. When the conventional dyes are conjugated with biomolecules such as protein, the fluorescence intensity of the labeled target is not directly to the number of attached dye molecules, but rather less than the predicted intensity due to self-quenching effect amongst the multiple dyes attached to the target. Second, the typical emission band half-width of the conventional dyes is about 40-80 nm. When using these conventional dyes for multiplex application, it is difficult to find a set of dyes whose emission spectra are spectrally resolved. Third, the low fluorescence quantum yield of conventional dyes decreases the detection sensitivity. All those limit the applications of conventional dyes.

Adding sulfonate groups to a dye has been shown to decrease the inherent tendency of the dye to form dimmers and aggregate, presumably due to the increased polar sulfonic acid moiety. See, e.g., U.S. Pat. Nos. 5,268,486, 6,977,305, and 6,130,101, and Panchuk-Voloshina, et al. J. Histochem. Cytochem. 47(9), 1179 (1999). Sulfonation increases the water solubility and the fluorescence brightness of carbocyanine dyes, but the photo-stability of carbocyanine dyes remains to be improved.

Rhodamine dyes with narrow fluorescence emission spectra can be obtained by the addition of chlorides to the phenyl group. For example, the emission spectra of dR110 is 10-15% narrower and has emission maxima at 10 nm longer wavelength than the unsubstituted R110. For more examples, see U.S. Pat. Nos. 5,847,162, 6,017,712, 6,025,505, 6,080,852, and 6,713,622, and L. G. Lee, et al. Nucleic Acids Res. 25(14), 2816 (1997). When using these 4,7-dichlororhodamine dyes to conjugate with proteins, these dyes are also prone to self-quenching by dimer formation.

The present invention describes 4,7-dichlororhodamine dyes that are substituted by at least one sulfonate moiety. The sulfonated 4,7-dichlororhodamine dyes of the invention possess considerable advantages over their non-sulfonated analogs, such as greater water solubility, and brighter fluorescence intensity. In particular, the sulfonated 4,7-dichlororhodamine dyes of the invention possess better photo-stability than those of other dyes having comparable spectra, such as cyanine dyes. In addition, the sulfonated 4,7-dichlororhodamine dyes of the invention exhibit resistance to quenching upon protein conjugation. Besides, the sulfonated 4,7-dichlororhodamine dyes of the invention are much easier to separate the 5-isomer and 6-isomer than the unsulfonated 4,7-dichlororhodamine dyes, due to good water solubility.

SUMMARY

The present invention describes 4,7-dichlororhodamine dyes that are substituted one or more times by a sulfonic acid, or a salt of a sulfonic acid that are useful as fluorescent probes. The dyes of the invention optionally possess a reactive group useful for preparing fluorescent conjugates. In addition, the dyes of the invention have higher water solubility, improved fluorescence quantum yield, and improved photo-stability. Besides, the labeled biomolecules prepared using the dyes of the invention show significantly reduced dimer formation.

The dyes of the invention are 4,7-dichlororhodamine dyes, that are substituted one or more times by —SO$_3$Y or —CH$_2$SO$_3$Y where Y is H or a counterion. The dyes of the invention generally have the formula:

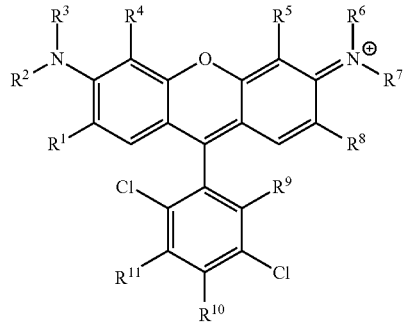

wherein:

R$^1$, R$^4$, R$^5$ and R$^8$ are independently hydrogen, —SO$_3$Y, C$_1$-C$_6$ alkyl, or C$_1$-C$_6$ alkoxy, where each alkyl or alkoxy is optionally further substituted by a carboxylic acid, a salt of carboxylic acid, or a carboxylic acid ester of a C$_1$-C$_6$ alcohol. Alternatively one or more of R$^1$, R$^4$, R$^5$ and R$^8$ are —SO$_3$Y. In a preferred embodiment, R$^4$ and R$^5$ are each —SO$_3$Y.

R$^2$, R$^3$, R$^6$ and R$^7$ are independently hydrogen, C$_1$-C$_6$ alkyl, C$_1$-C$_6$ carboxyalkyl, C$_1$-C$_6$ sulfoalkyl, a salt of C$_1$-C$_6$ carboxyalkyl, or a salt of C$_1$-C$_6$ sulfoalkyl, wherein the alkyl portions each are independently and optionally substituted by amino, hydroxyl, carboxylic acid, a salt of carboxylic acid, or a carboxylic acid ester of a C$_1$-C$_6$ alcohol.

Or R$^2$ in combination with R$^1$, or R$^3$ in combination with R$^4$, or both, form a 5- or 6-membered ring that is saturated or unsaturated, and is optionally substituted by one or more C$_1$-C$_6$ alkyls, or —CH$_2$SO$_3$Y moieties.

Or R$^6$ in combination with R$^5$, or R$^7$ in combination with R$^8$, or both, form a 5- or 6-membered ring that is saturated or unsaturated, and is optionally substituted by one or more C$_1$-C$_6$ alkyls, or —CH$_2$SO$_3$Y moieties.

R$^9$ is carboxylate or sulfonate. R$^{10}$ and R$^{11}$ are independently hydrogen, Cl, or R$_x$, where R$_x$ is a reactive group. In a preferred embodiment, R$^9$ is carboxylate, one of R$^{10}$ and R$^{11}$ is hydrogen and the other is R$_x$.

DETAILED DESCRIPTION

Figure 1:
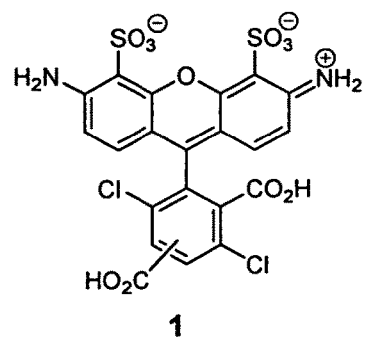
FIG. 1: The structures of several preferred dye compounds 1, 2, 4, 7, 8, 9 of the present invention.
Figure 1:
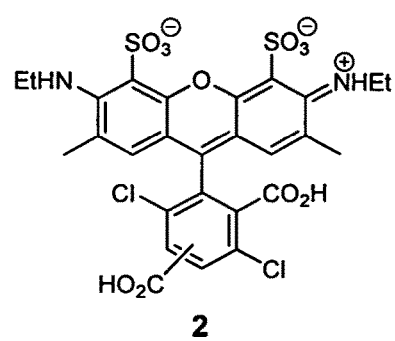
Figure 1:
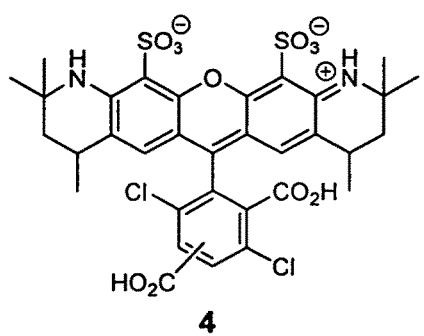
Figure 1:
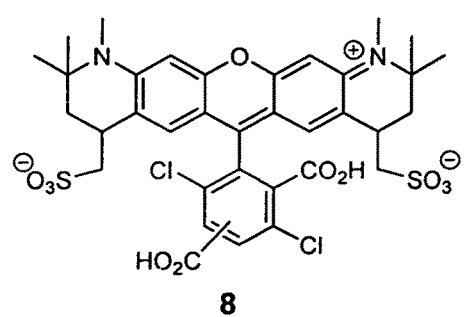
Figure 1:
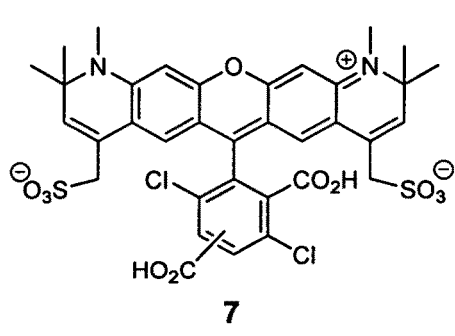
Figure 1:
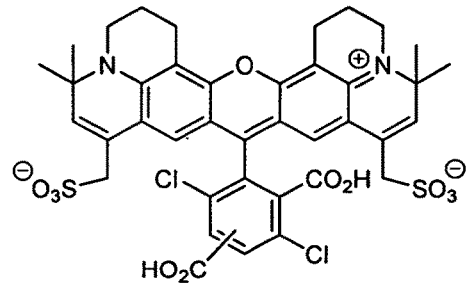
Figure 2:
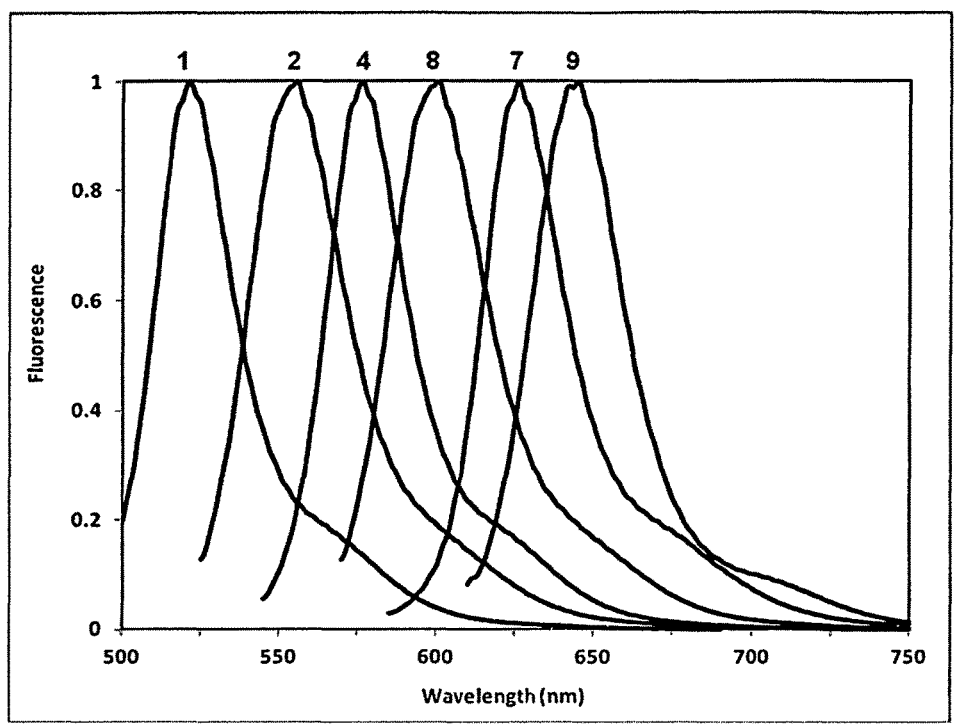
FIG. 2: The fluorescence emission spectra of several preferred dye compounds 1, 2, 4, 7, 8, 9 of the present invention.
Figure 3:
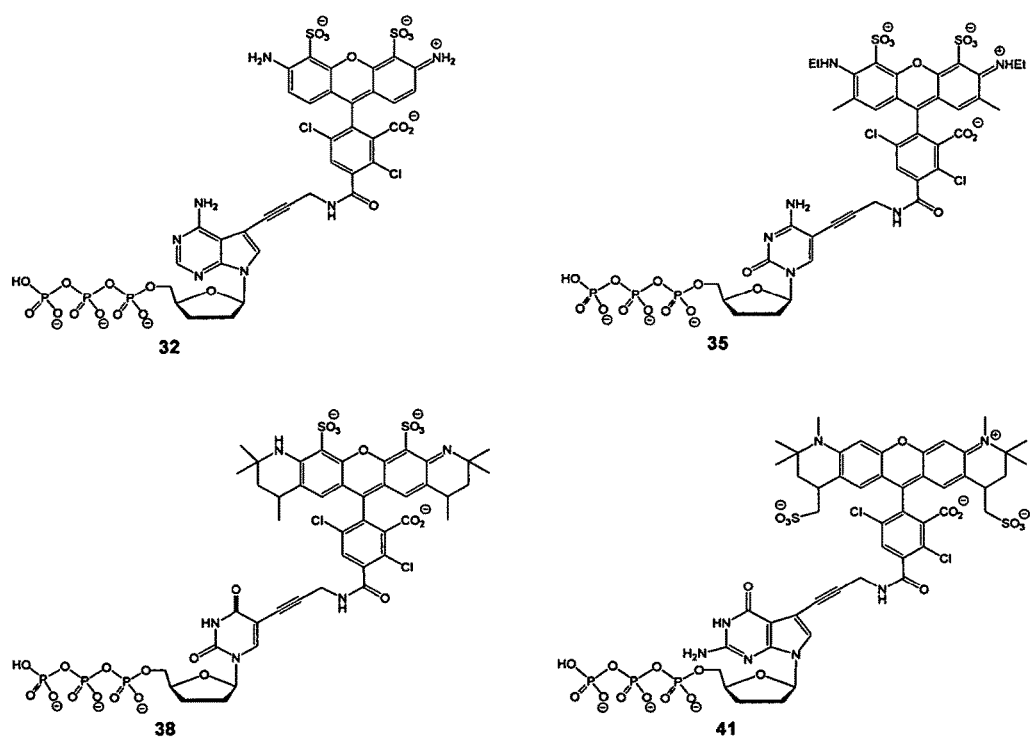
FIG. 3: The structures of several dye-labeled nucleotides 32, 35, 38, 41 of the present invention.
Figure 4:
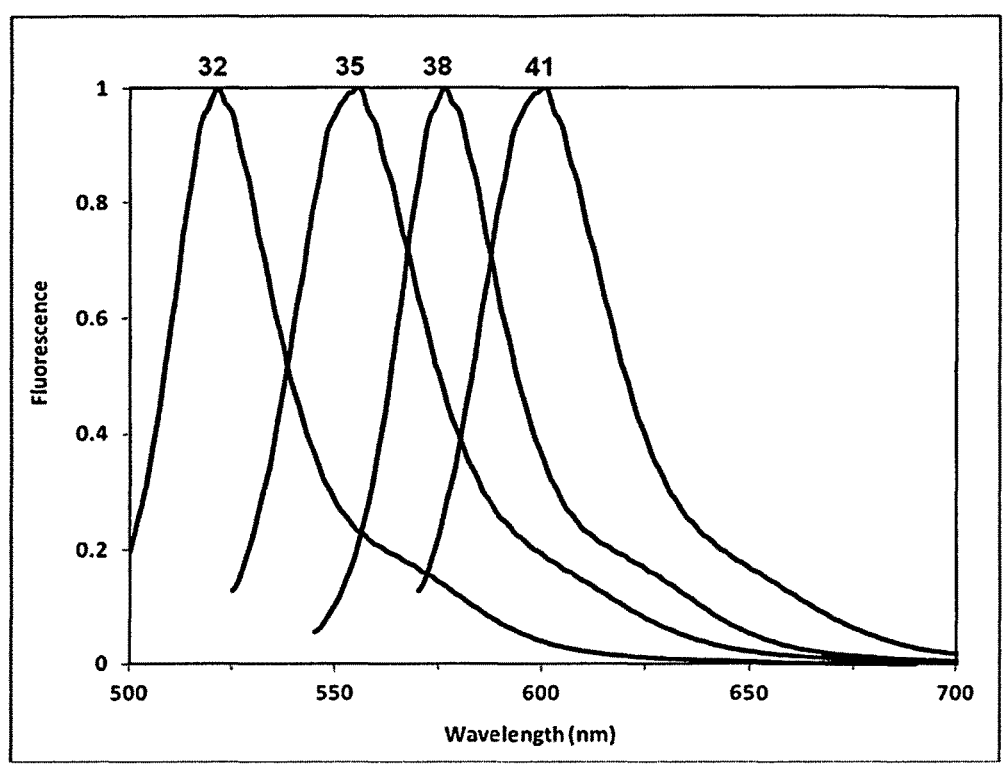
FIG. 4: The fluorescence emission spectra of several dye-labeled nucleotides 32, 35, 38, 41 of the present invention.

Fluorescent dyes are used in various biological applications, such as protein and nucleic acid labeling, for example. Methods associated with fluorescent dyes, such as methods of use thereof, for example, are also useful. The present invention describes 4,7-dichlororhodamine dyes that are substituted one or more times by a sulfonic acid, or a salt of a sulfonic acid that are useful as fluorescent probes. The fluorescent dyes of the invention with sulfonate substitute groups have higher water solubility, improved fluorescence quantum yield, and improved photo-stability. Besides, the labeled biomolecules prepared using the dyes of the invention show significantly reduced dimer formation. In addition, the sulfonated 4,7-dichlororhodamine dyes have narrow emission spectra with great advantage in multiplex application, such as immunoassay and DNA sequencing, for example. The dyes of the invention optionally possess a reactive group useful for preparing fluorescent conjugates, which conjugates and methods for their preparation and use are described herein.

In one embodiment, the dyes of the invention are 4,7-dichlororhodamine dyes, that are substituted one or more times by —$SO_3Y$ or —$CH_2SO_3Y$ where Y is H or a counterion. The dyes of the invention generally have the formula:

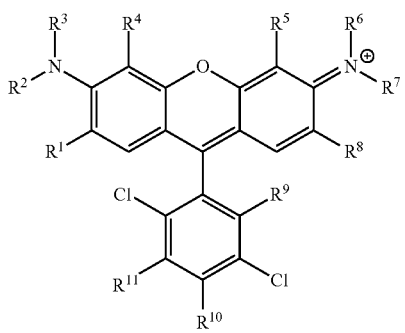

wherein:

$R^1$, $R^4$, $R^5$ and $R^8$ are independently hydrogen, $C_1$-$C_6$ alkyl, or $C_1$-$C_6$ alkoxy, where each alkyl or alkoxy is optionally further substituted by a carboxylic acid, a salt of carboxylic acid, or a carboxylic acid ester of a $C_1$-$C_6$ alcohol. Alternatively one or more of $R^1$, $R^4$, $R^5$ and $R^8$ are —$SO_3Y$. In a preferred embodiment, $R^4$ and $R^5$ are each —$SO_3Y$.

$R^2$, $R^3$, $R^6$ and $R^7$ are independently hydrogen, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions each are independently and optionally substituted by amino, hydroxyl, carboxylic acid, a salt of carboxylic acid, or a carboxylic acid ester of a $C_1$-$C_6$ alcohol.

In one embodiment of the invention, $R^2$ in combination with $R^1$, or $R^3$ in combination with $R^4$, or both, form a 5- or 6-membered ring that is saturated or unsaturated, and is optionally substituted by one or more $C_1$-$C_6$ alkyls, or —$CH_2SO_3Y$ moieties. In another embodiment of the invention, $R^6$ in combination with $R^5$, or $R^7$ in combination with $R^8$, or both, form a 5- or 6-membered ring that is saturated or unsaturated, and is optionally substituted by one or more $C_1$-$C_6$ alkyls, or —$CH_2SO_3Y$ moieties. Some examples of fused 6-membered rings as described herein are provided below.

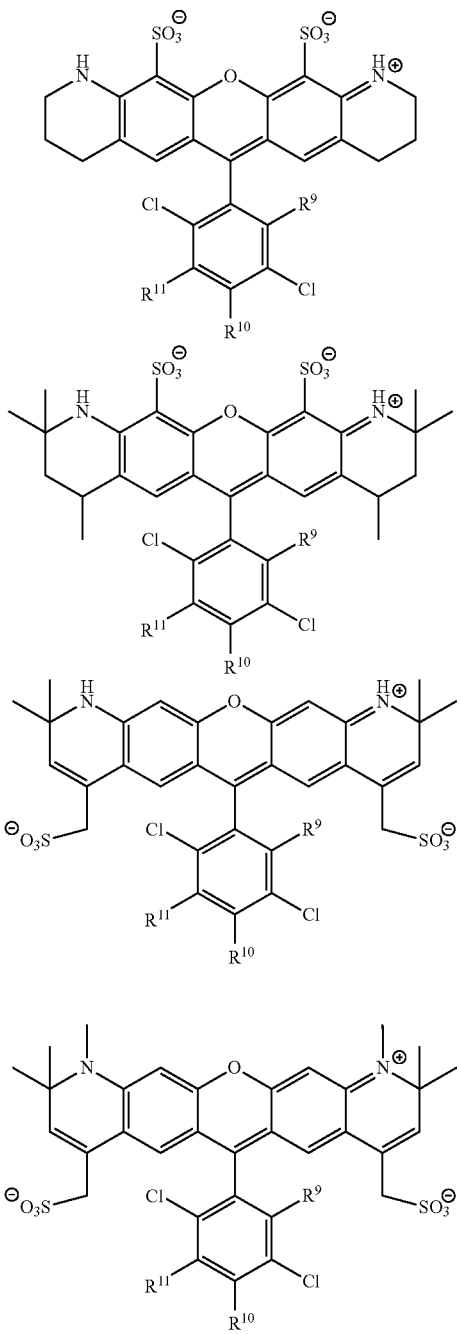

-continued

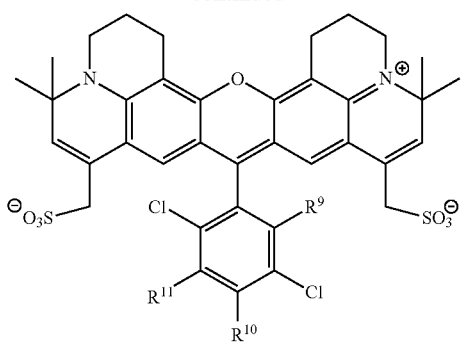

$R^9$ is carboxylate or sulfonate. $R^{10}$ and $R^{11}$ are independently hydrogen, Cl, or $R_x$, where $R_x$ is a reactive group. In a preferred embodiment, $R^9$ is carboxylate, one of $R^{10}$ and $R^{11}$ is hydrogen and the other is R. Some examples of $R_x$ as described herein are provided below.

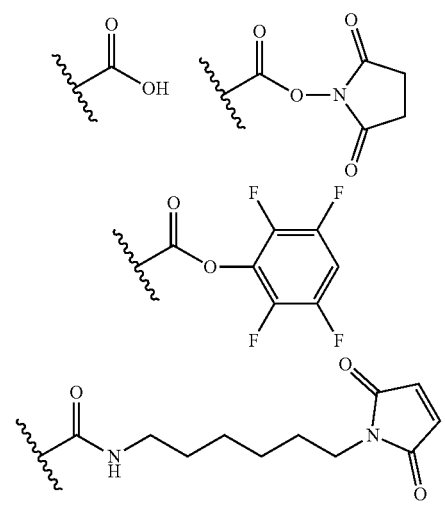

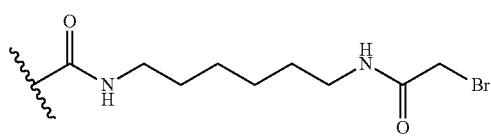

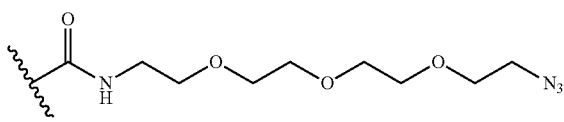

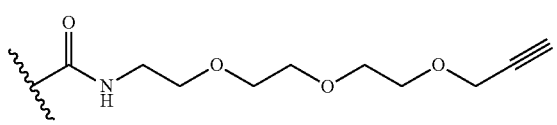

In one embodiment, a method of labeling a nucleotide with the sulfonated 4,7-dichlororhodamine dyes of the invention is provided. The labeled nucleotides of the invention generally have the formula:

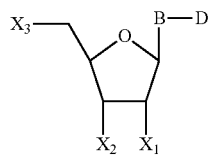

wherein:
B is a uracil, cytosine, deazaadenine, or deazaguanosine.
D is the sulfonated 4,7-dichlororhodamine dye described above.
$X_1$ and $X_2$ are independently H or OH.
$X_3$ is OH, $OPO_3^-$, $OP_2O_6^{2-}$, or $OP_3O_9^{3-}$.

In one preferred embodiment, the nucleotides of the invention are dideoxynucleotide triphosphates having the formula:

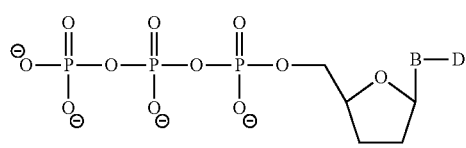

Labeled dideoxynucleotides as shown above have particular application in chain terminating reaction in Sanger DNA sequencing application.

In another preferred embodiment, the nucleotides of the invention are deoxynucleotide triphosphates having the formula:

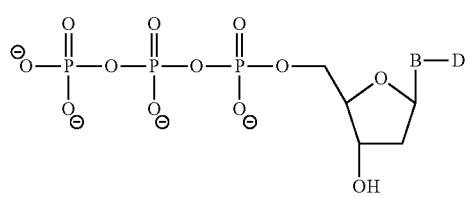

Labeled deoxynucleotides as shown above have particular application in the polymerase chain reaction.

In one embodiment, a method of labeling a biomolecule with the sulfonated 4,7-dichlororhodamine dyes of the invention is provided. The biomolecules can be an amino acid, peptide, protein, antibody, polysaccharide, nucleotide, nucleic acid, hapten, drug, lipid, polymer, cell, bacterium, yeast, or virus. Preferably, the biomolecules are protein, antibody, or nucleic acid. The dyes used in the invention possesses a reactive group having the formula:

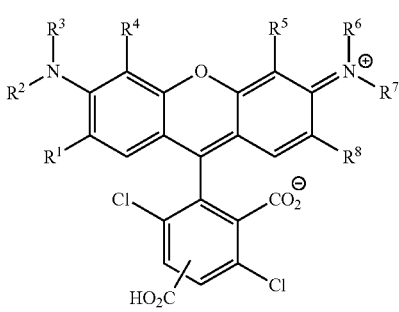

In one embodiment, a kit for labeling of biomolecules with the dyes of the invention is provided. The kit comprises the fluorescent dye as described above, and information concerning use of the fluorescent dye. The kit may comprise, optionally, labeling buffer, purification columns, or purification resin. The dyes used in the invention possesses a reactive group having the formula:

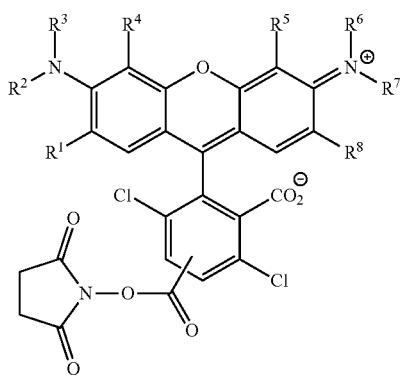

Certain nonlimiting exemplary sulfonated 4,7-dichlororhodamine dyes are shown in Tables 1.

TABLE 1

Nonlimiting exemplary sulfonated 4,7-dichlororhodamine dye structures

TABLE 1-continued

Nonlimiting exemplary sulfonated 4,7-dichlororhodamine dye structures

TABLE 1-continued

Nonlimiting exemplary sulfonated 4,7-dichlororhodamine dye structures

| Compound | Structure |
| --- | --- |
| 8 | 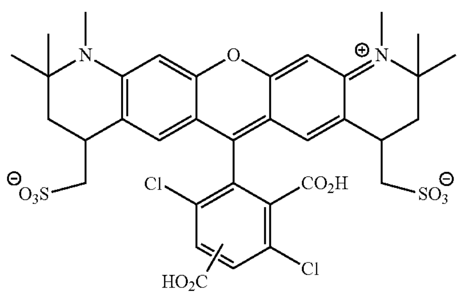 |
| 9 | 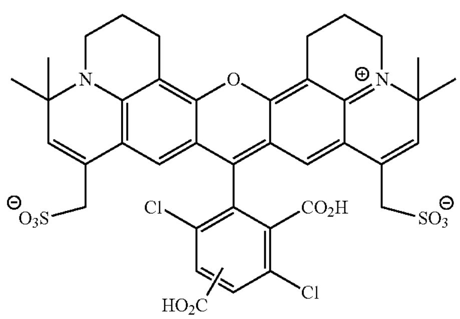 |
| 10 | 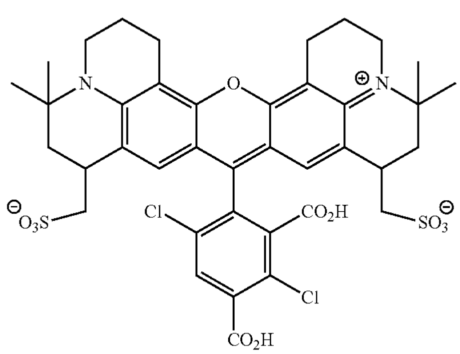 |

EXAMPLES

The examples discussed below are intended to be purely exemplary of the invention and should not be considered to limit the invention in any way. The examples are not intended to represent that the experiments below are all or the only experiments performed.

Example 1

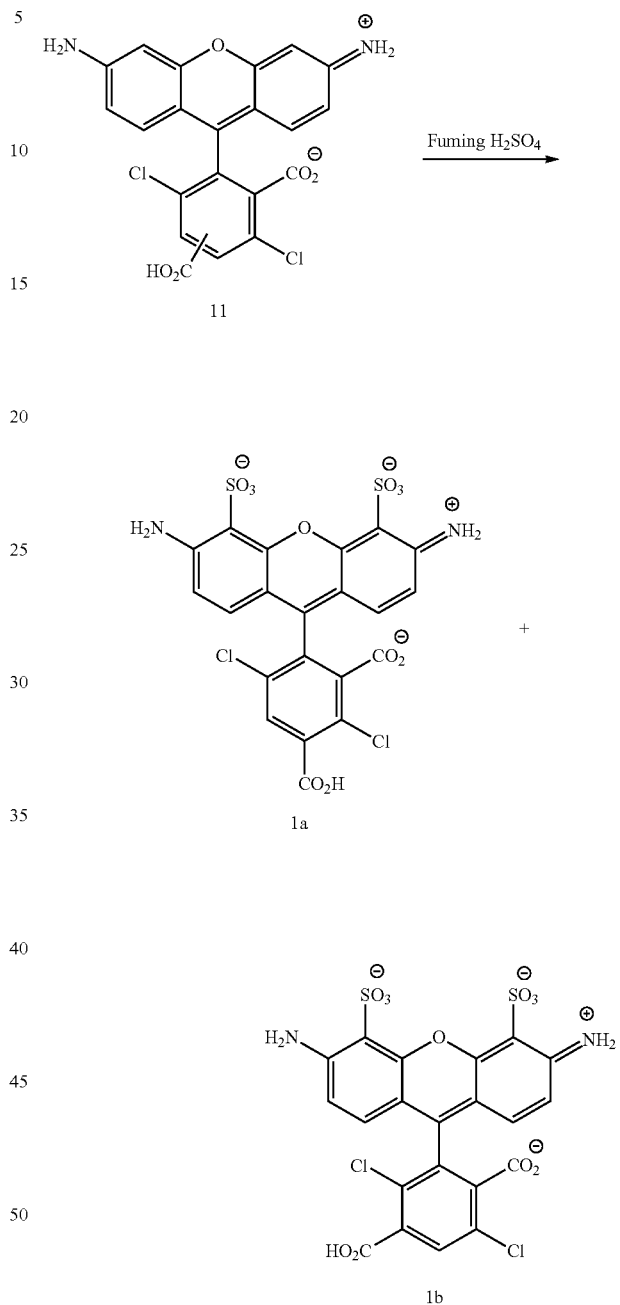

Preparation of Compound (1a and 1b)

Place ~5 mL fuming $H_2SO_4$ in a 50 mL round bottom flask and cool in an ice/water bath. Compound 11 (200 mg, 0.45 mmol) is added, and the reaction mixture is stirred at 0° C. until TLC shows complete consumption of compound 11. The mixture is added to the stirring $Et_2O$ solution (~300 mL) at 0° C. The resulting precipitate is filtered, washed with EtOAc, and dried. The crude product is purified by RP-HPLC using TEAA/ACN to give compound 1a (90 mg, 25%) and compound 1b (98 mg, 27%).

Example 2

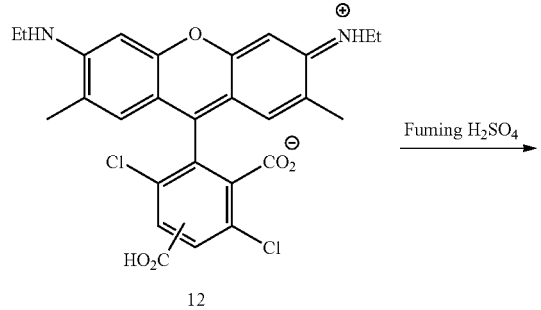

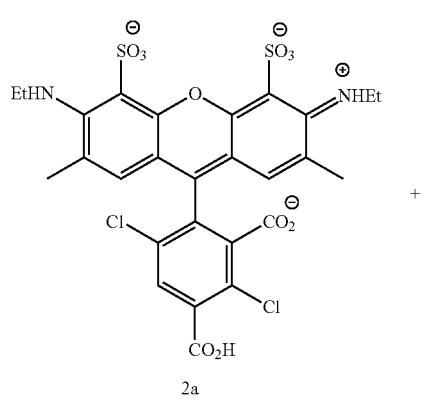

Compound 2a and 2b is prepared in a method analogous to that of compound 1a and 1b, above.

Example 3

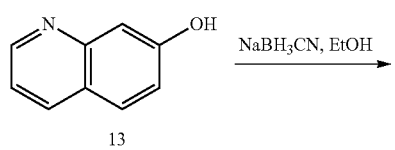

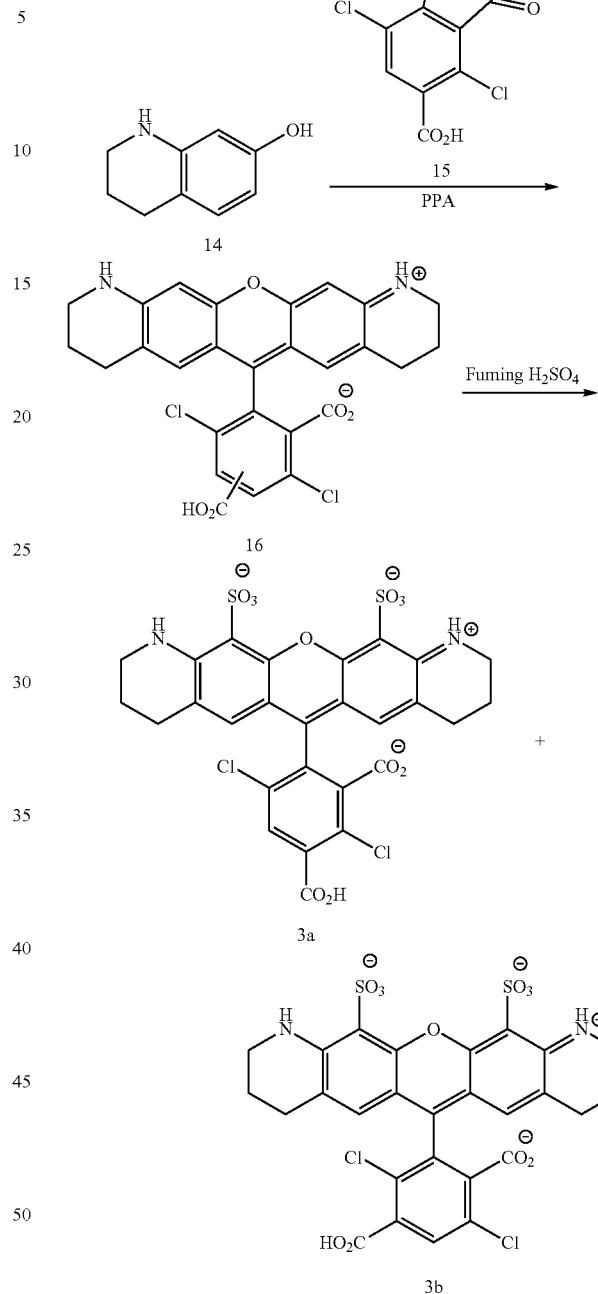

Preparation of Compound (14)

To a solution of 7-hydroxyquinoline (2 g, 13.8 mmol) in 30 mL EtOH is added NaCNBH₃ (3.5 g, 55 mmol) in portions. After stirring at room temperature for 4 hr, the mixture is concentrated, extracted with EtOAc, and washed with brine. The organic layer is dried over Na₂SO₄ and evaporated. The crude product is purified on silica gel using hexane/EtOAc. Yield: 1.44 g (70%).

Preparation of Compound (16)

A mixture of compound 14 (1 g, 6.7 mmol) and 3,6-dichlorotrimellitic anhydride (875 mg, 3.35 mmol) in 5 mL polyphosphoric acid is heated to 180° C. overnight. After cooling to room temperature, the mixture is poured into ice/water, and stirred for 30 min. The resulting precipitate is filtered, washed with water, and dried under vacuum. The crude product is purified on silica gel using CH$_2$Cl$_2$/MeOH. Yield: 438 mg (25%).

Preparation of Compound (3a and 3b)

Compound 3a and 3b is prepared in a method analogous to that of compound 1a and 1b, above.

Example 4

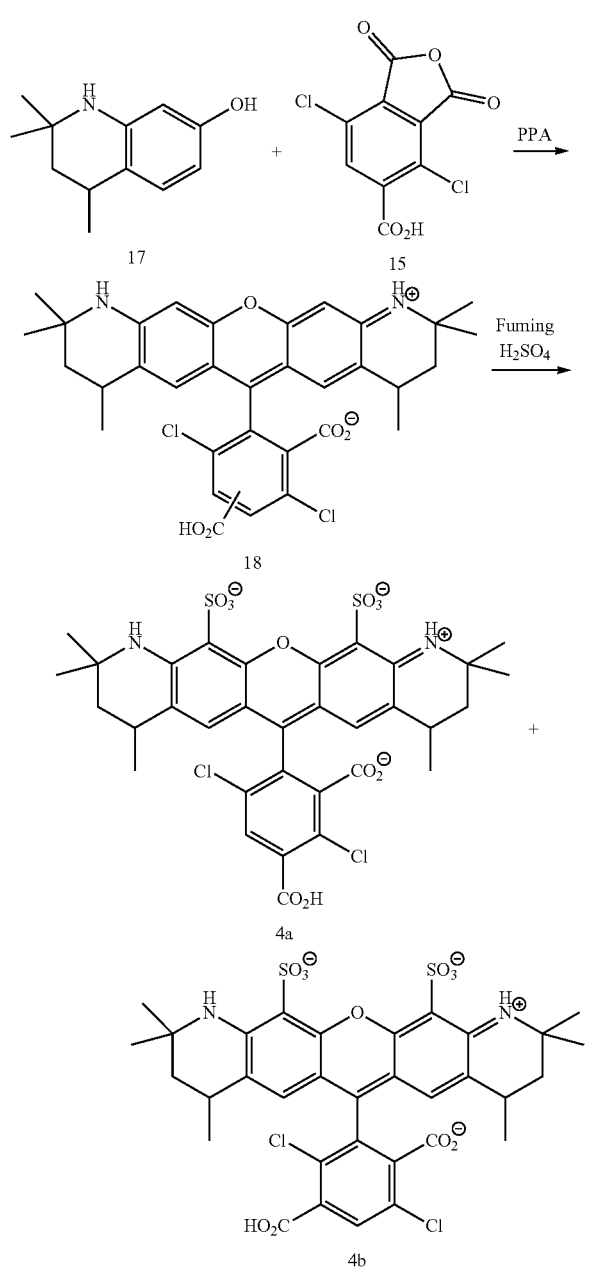

Preparation of Compound (18)

Compound 18 is prepared in a method analogous to that of compound 16, above.

Preparation of Compound (4a and 4b)

Compound 4a and 4b is prepared in a method analogous to that of compound 1a and 1b, above.

Example 5

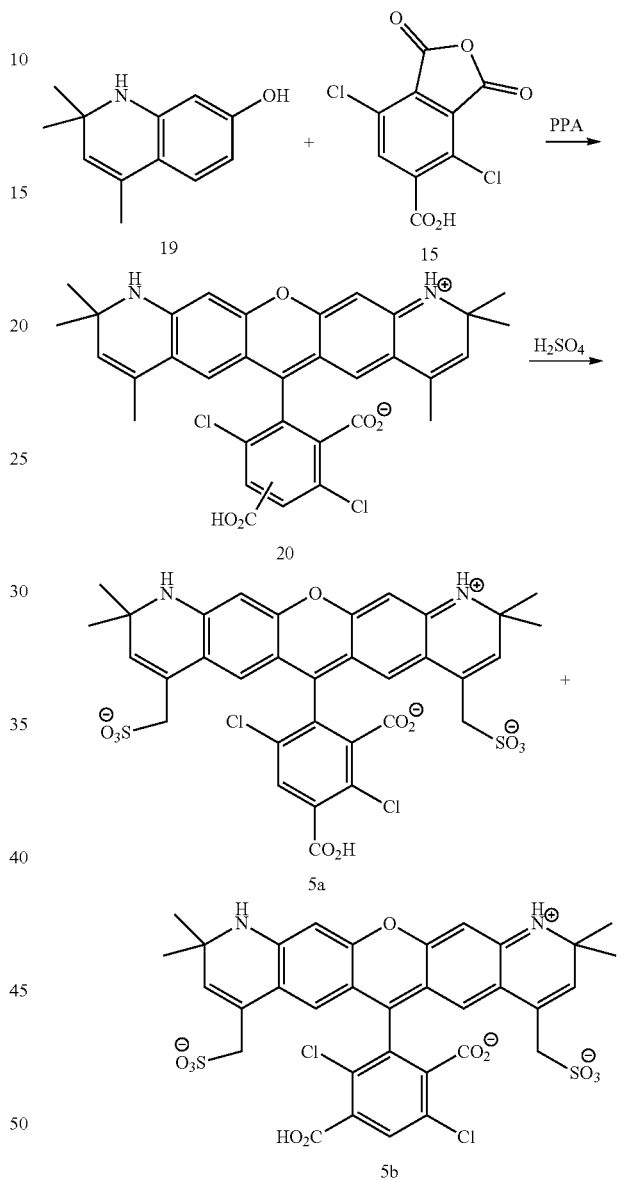

Preparation of Compound (20)

Compound 20 is prepared in a method analogous to that of compound 16, above.

Preparation of Compound (5a and 5b)

Place 5 mL concentrated H$_2$SO$_4$ in a 50 mL round bottom flask and cool in an ice/water bath. Compound 20 (300 mg, 0.5 mmol) is added in portions, and the reaction mixture is stirred at room temperature until TLC shows complete consumption of compound 20. The mixture is added to the stirring Et$_2$O solution (~400 mL) at 0° C. The resulting precipitate is filtered, washed with EtOAc, and dried. The crude product is purified by RP-HPLC using TEAA/ACN give compound 5a (96 mg, 20%) and compound 5b (101 mg, 21%).

Example 6

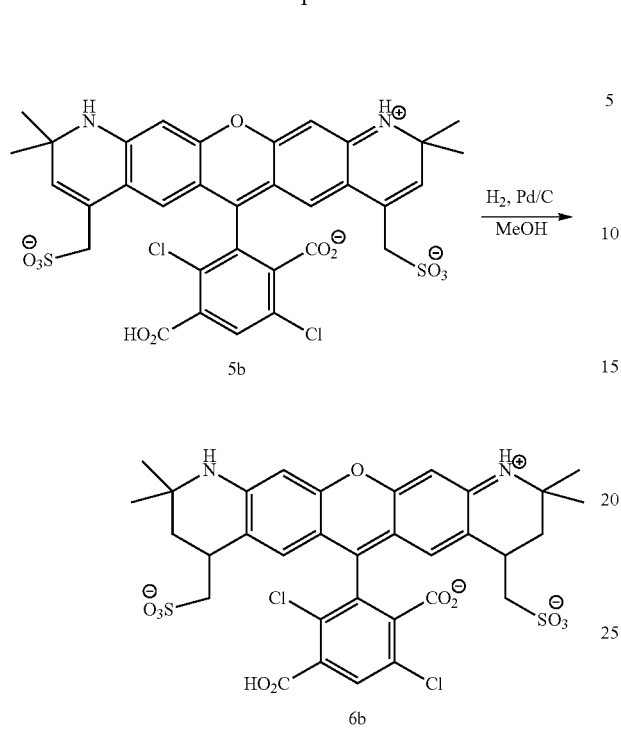

Compound 5b (100 mg, 0.1 mmol) is dissolved in 10 mL MeOH, 10% Pd/C (~50 mg) is added under argon. The reaction mixture is bubbled with $H_2$. The reaction is monitored by HPLC. After the reaction is complete, the mixture is filtered through celite, and concentrated. The crude product is purified by RP-HPLC using TEAA/ACN give compound 6b (71 mg, 70%)

Example 7

Preparation of Compound (22)
Compound 22 is prepared in a method analogous to that of compound 16, above.

Preparation of Compound (7a and 7b)
Compound 7a and 7b is prepared in a method analogous to that of compound 5a and 5b, above.

Example 8

Preparation of Compound (8b)
Compound 8b is prepared in a method analogous to that of compound 6b, above.

Example 9

[Structures of compounds 23, 15, and 24 with reaction scheme using PPA and H₂SO₄]

Preparation of Compound (24)

Compound 24 is prepared in a method analogous to that of compound 16, above.

Preparation of Compound (9a and 9b)

Compound 9a and 9b is prepared in a method analogous to that of compound 5a and 5b, above.

Example 10

[Structure of compound 9b with H₂, Pd/C, MeOH reaction to give 10b]

Preparation of Compound (10b)

Compound 10b is prepared in a method analogous to that of compound 6b, above.

Example 11

[Structure of compound 1a with TSTU, TEA, DMF]

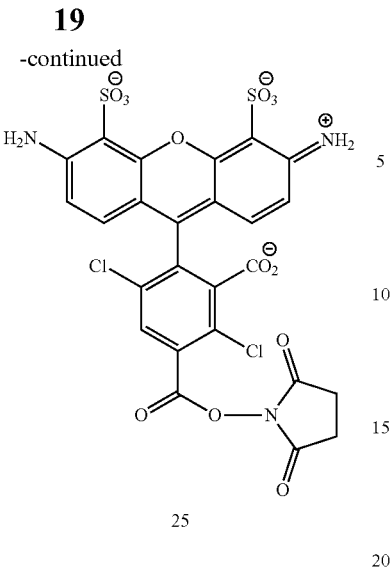

25

Preparation of Compound (25)

The general method of converting the acid to its N-hydroxysuccinimide is exampled as follows. Compound 1a (1 mmol) is dissolved in anhydrous DMF (5 mL). TSTU (1.1 mmol) and TEA (1.5 mmol) are added, then the reaction mixture is stirred at room temperature until TLC indicates the reaction is complete. Ethyl acetate (50 mL) is added to the reaction mixture and stirred for 30 min. The resulting precipitate is filtered, washed with ethyl acetate, acetone, then dired to give compound 25.

Example 12

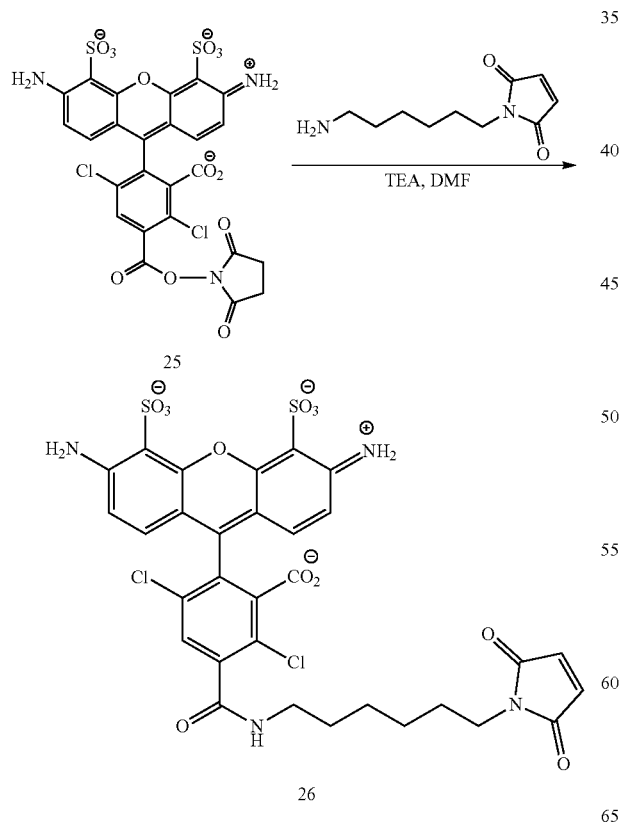

26

Preparation of Compound (26)

The general method to make maleimide derivatives is exampled as follows. Compound 25 (1 mmol) is dissolved in anhydrous DMF (5 mL). N-(6-aminohexyl)maleimide (1.2 mmol) and TEA (1.5 mmol) are added, then the reaction mixture is stirred at room temperature for 1 hr. Ethyl acetate (50 mL) is added to the reaction mixture and stirred for 30 min. The resulting precipitate is filtered, washed with ethyl acetate, acetone, then dired. The crude product is purified by RP-HPLC using TEAA/ACN.

Example 13

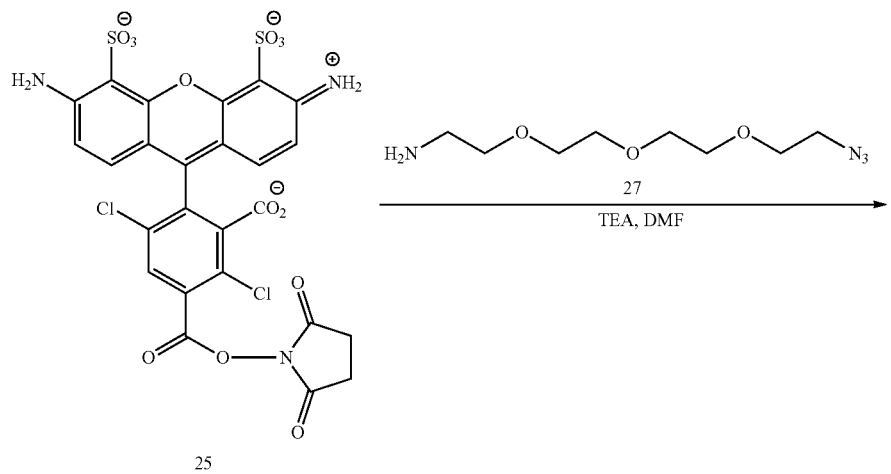

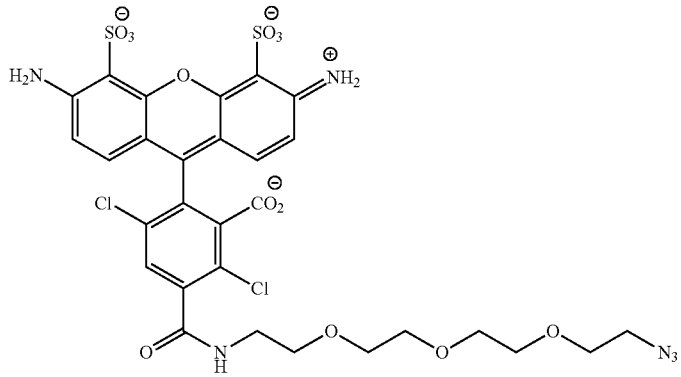

Preparation of Compound (28)

The general method to make azide derivatives is exampled as follows. Compound 25 (1 mmol) is dissolved in anhydrous DMF (5 mL). Compound 27 (1.2 mmol) and TEA (1.5 mmol) are added, then the reaction mixture is stirred at room temperature for 1 hr. Ethyl acetate (50 mL) is added to the reaction mixture and stirred for 30 min. The resulting precipitate is filtered, washed with ethyl acetate, acetone, then dired. The crude product is purified by RP-HPLC using TEAA/ACN.

23
Example 14

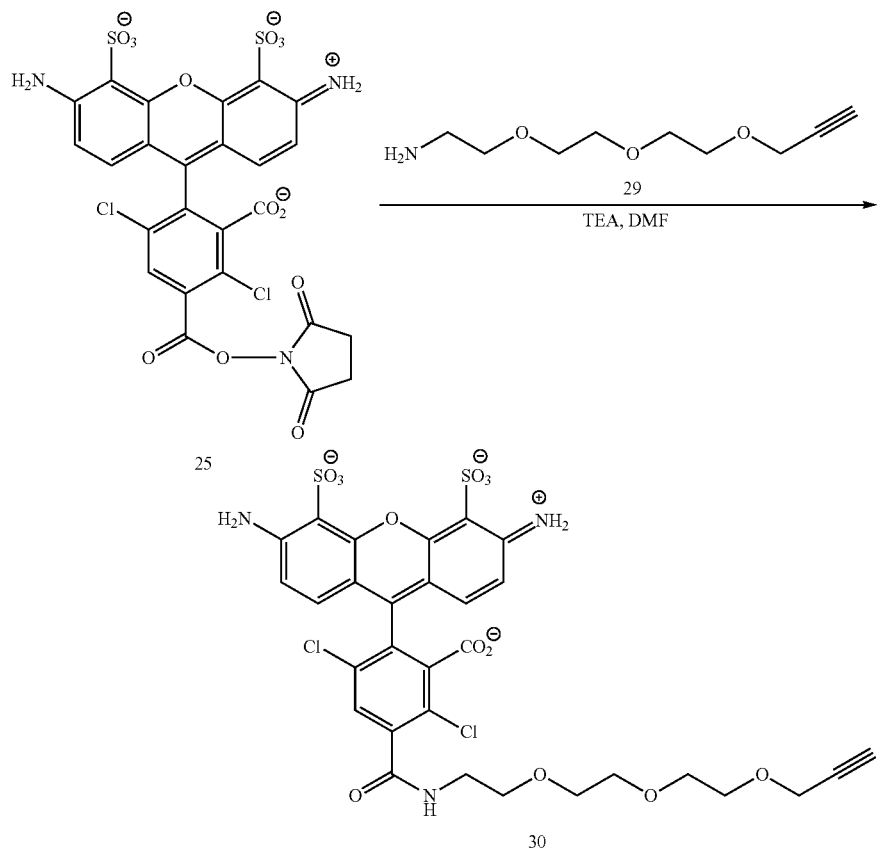

Preparation of Compound (30)

The general method to make alkyne derivatives is exampled as follows. Compound 25 (1 mmol) is dissolved in anhydrous DMF (5 mL). Compound 29 (1.2 mmol) and TEA (1.5 mmol) are added, then the reaction mixture is stirred at room temperature for 1 hr. Ethyl acetate (50 mL) is added to the reaction mixture and stirred for 30 min. The resulting precipitate is filtered, washed with ethyl acetate, acetone, then dired. The crude product is purified by RP-HPLC using TEAA/ACN.

Example 15

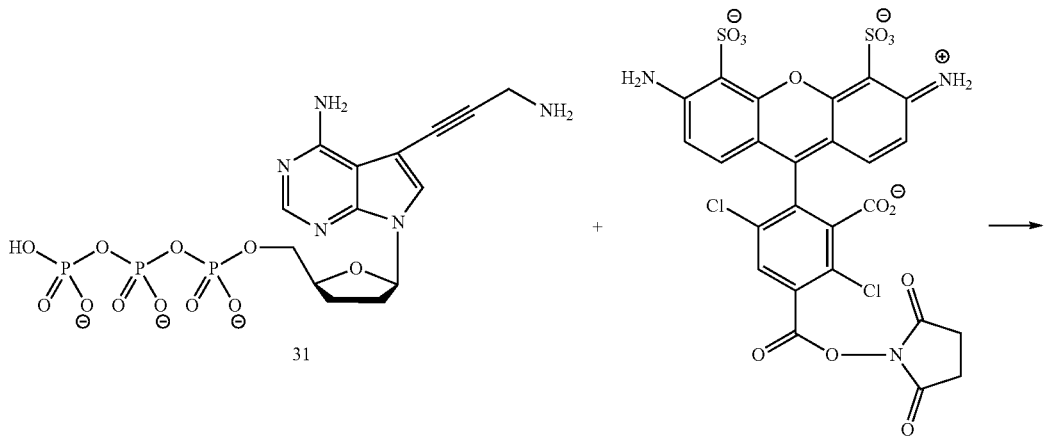

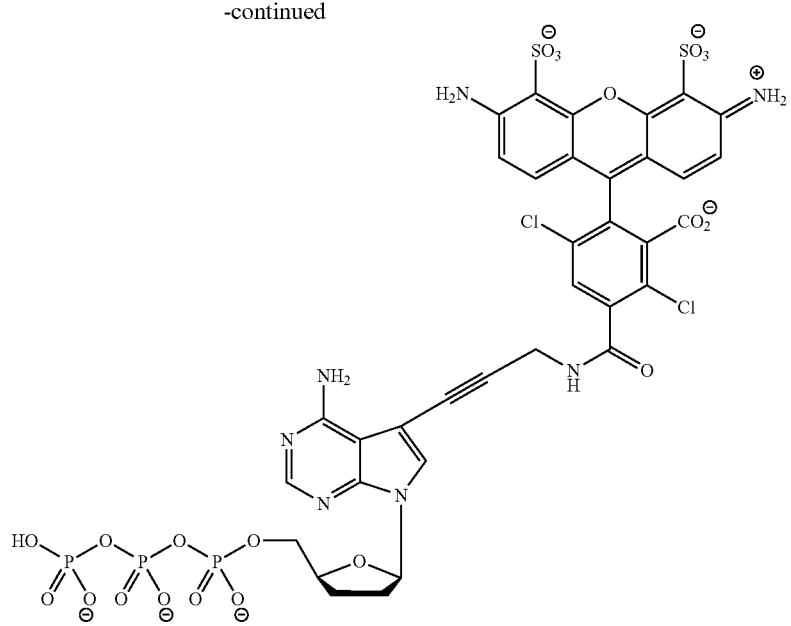

Preparation of Compound (32)

Compound 31 (10 μmol) is dissolved in 0.1 M sodium borate (2 mL), pH 8.5. Compound 25 (15 μmol) in DMSO is added, then the reaction mixture is stirred at room temperature for 1 hr. The mixture is subjected to HPLC with an anion-exchange column to remove free dye, then subjected to a second HPLC using a reverse-phase HPLC column. The solutions containing dye-labeled nucleotide are concentrated in a vacuum centrifuge to give compound 32.

Example 16

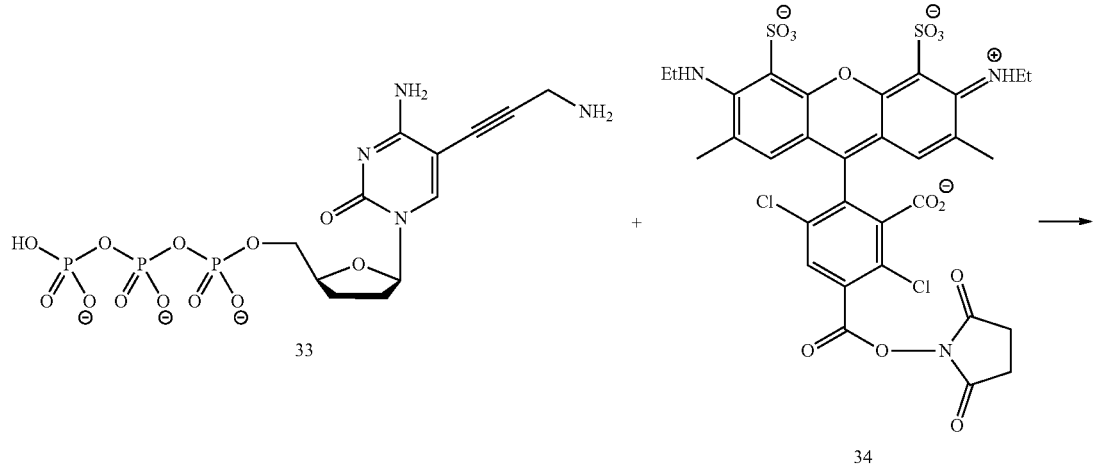

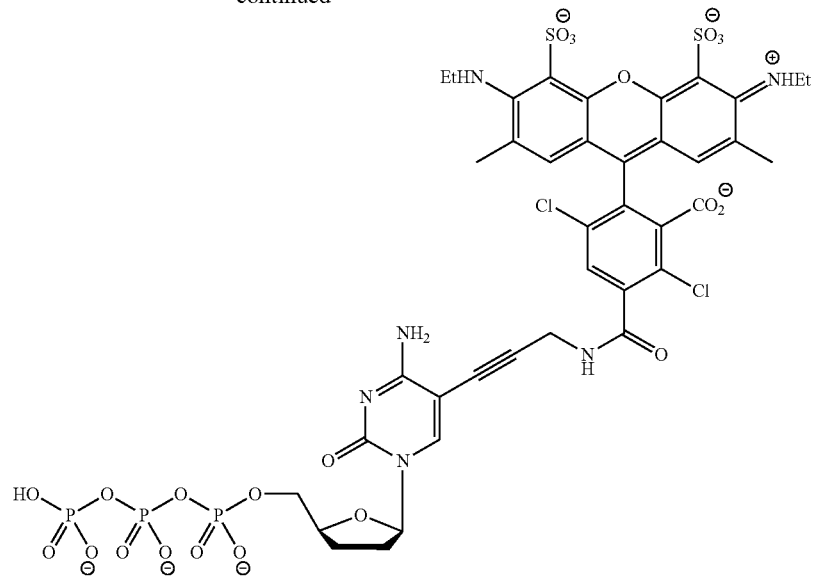

35

Preparation of Compound (35)

Compound 33 (10 μmol) is dissolved in 0.1 M sodium borate (2 mL), pH 8.5. Compound 34 (15 μmol) in DMSO is added, then the reaction mixture is stirred at room temperature for 1 hr. The mixture is subjected to HPLC with an anion-exchange column to remove free dye, then subjected to a second HPLC using a reverse-phase HPLC column. The solutions containing dye-labeled nucleotide are concentrated in a vacuum centrifuge to give compound 35.

Example 17

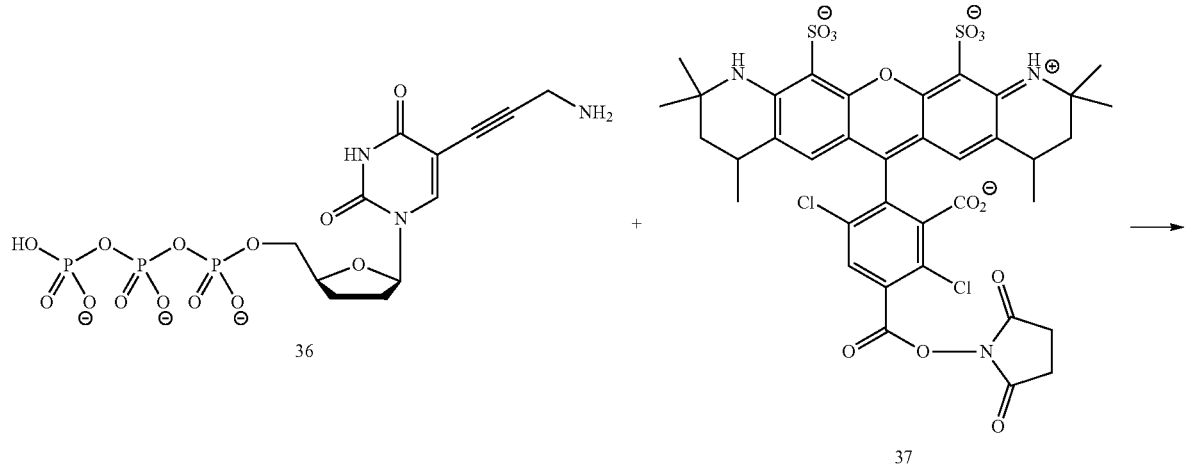

36 + 37

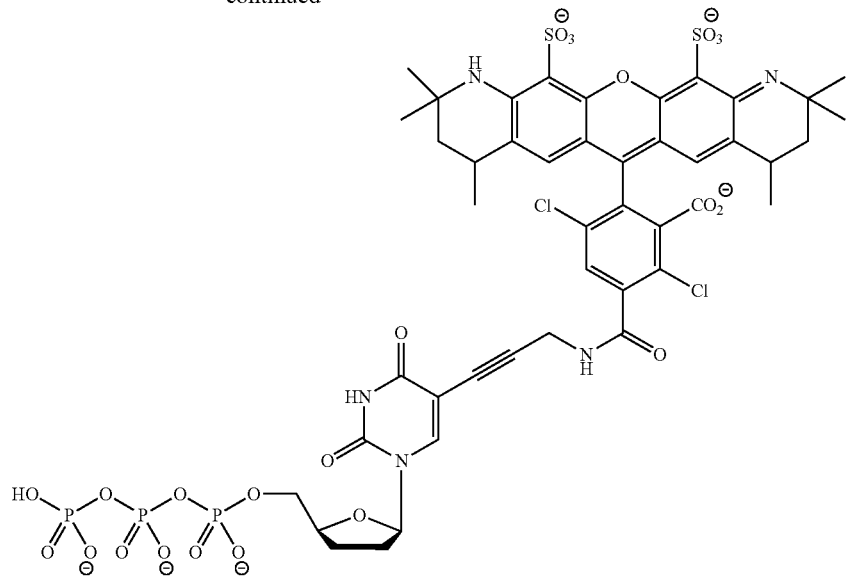

38

Preparation of Compound (38)

Compound 36 (10 μmol) is dissolved in 0.1 M sodium borate (2 mL), pH 8.5. Compound 37 (15 μmol) in DMSO is added, then the reaction mixture is stirred at room temperature for 1 hr. The mixture is subjected to HPLC with an anion-exchange column to remove free dye, then subjected to a second HPLC using a reverse-phase HPLC column. The solutions containing dye-labeled nucleotide are concentrated in a vacuum centrifuge to give compound 38.

Example 18

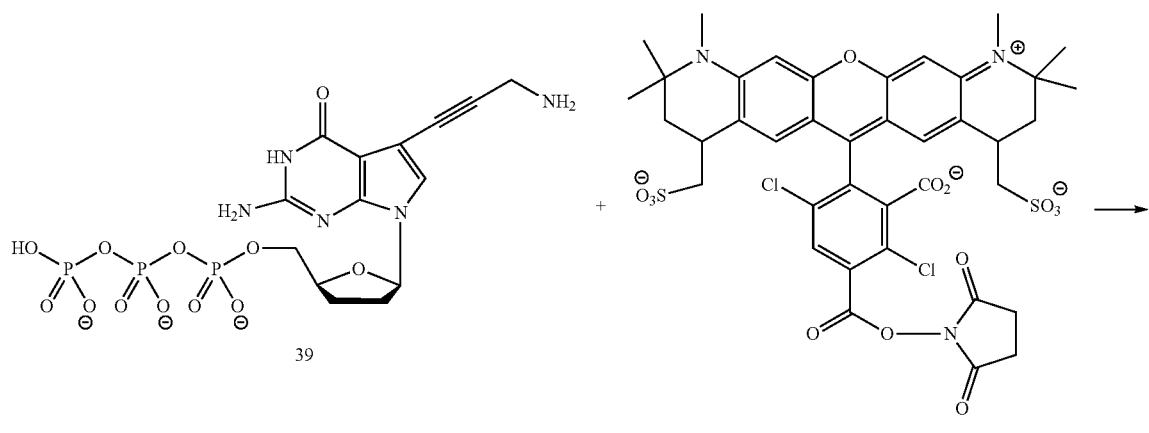

39 + 40 →

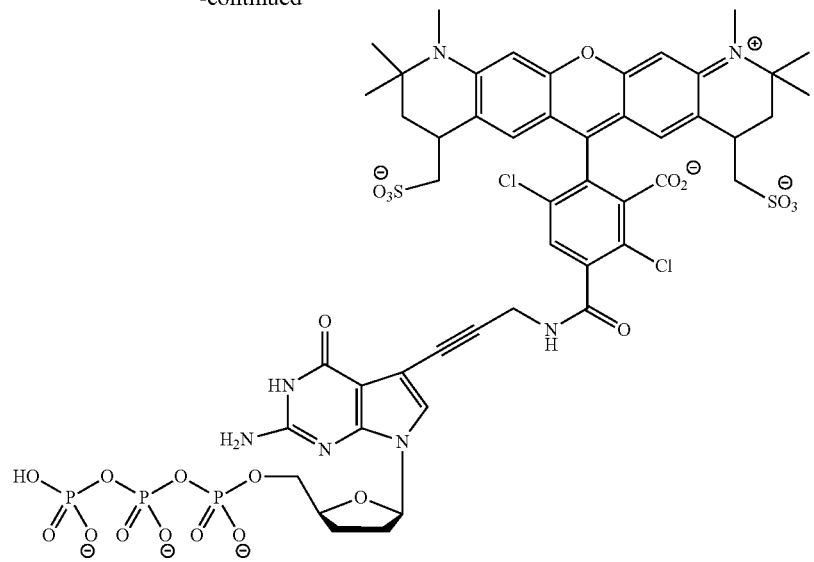

41

Preparation of Compound (41)

Compound 39 (10 μmol) is dissolved in 0.1 M sodium borate (2 mL), pH 8.5. Compound 40 (15 μmol) in DMSO is added, then the reaction mixture is stirred at room temperature for 1 hr. The mixture is subjected to HPLC with an anion-exchange column to remove free dye, then subjected to a second HPLC using a reverse-phase HPLC column. The solutions containing dye-labeled nucleotide are concentrated in a vacuum centrifuge to give compound 41.

Example 19

Oligonucleotide labeling: A 5'-amino modified oligonucleotide (100 nmol) is dissolved in 100 μL water. 10 μL of 1 M NaHCO$_3$ is added. Then, the reactive succinimidyl ester of dye (1 μmol) in DMSO is added. After overnight, 1 mL ethanol is added. The mixture is cooled at −20° C., centrifuged, and the supernatant is decanted. The pellet is rinsed with ethanol, and then dissolved in 100 μL water. The labeled oligonucleotide is purified by RP-HPLC using TEAA/ACN. The desired peak is collected and evaporated to give the fluorescent oligonucleotide.

Example 20

Protein and antibody labeling: A series of dye conjugates of streptavidin or goat anti-mouse IgG antibody are prepared using the reactive succinimidyl ester of dyes described above as follows.

A solution of the desired protein is prepared at 10 mg/ml in 0.1 M NaHCO$_3$. The reactive dyes are dissolved in DMSO at 10 mg/mL. Predetermined amounts of reactive dyes are added to the protein solution with stirring. The reaction mixture is incubated at room temperature for 1 hr. The dye-protein conjugate is separated from free unreacted dye by size-exclusion chromatography using BioGel P30 equilibrated with PBS. The initial, protein-containing colored band is collected and the degree of substitution is determined from the absorbance at the absorbance maximum of each fluorophore.

The invention claimed is:

1. A compound having the formula:

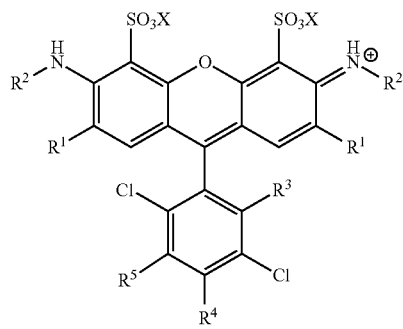

wherein:

R$^1$ and R$^2$ are independently hydrogen, or C$_1$-C$_6$ alkyl,

X is H or a counterion,

R$^3$ is carboxylate or sulfonate,

R$^4$ and R$^5$ are independently hydrogen, Cl, or R$_x$, where R$_x$ is a reactive group.

2. The compound according to claim 1, wherein R$^3$ is carboxylate.

3. The compound according to claim 2, wherein one of R$^4$ and R$^5$ is hydrogen and the other is R$_x$.

4. The compound according to claim 3, wherein R$^1$ and R$^2$ are hydrogen.

5. The compound according to claim 3, wherein R$^1$ is methyl, and R$^2$ is ethyl.

6. A compound having the formula:

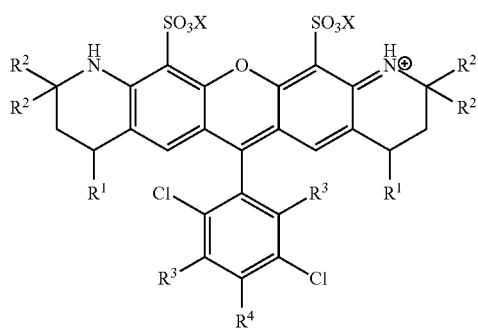

wherein:
$R^1$ and $R^2$ are independently hydrogen, or $C_1$-$C_6$ alkyl;
X is H or a counterion;
$R^3$ is carboxylate;
One of $R^4$ and $R^5$ is hydrogen and the other is Cl or $R_x$, where $R_x$ is a reactive group.

7. The compound according to claim 6, wherein $R^1$ and $R^2$ are hydrogen, or methyl.

8. A compound having the formula:

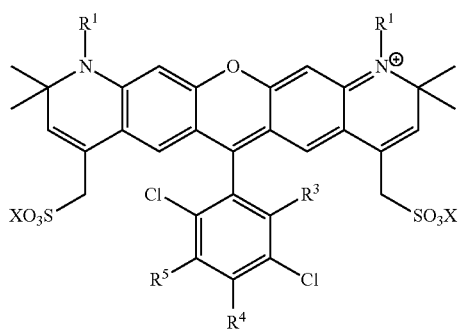

or the formula:

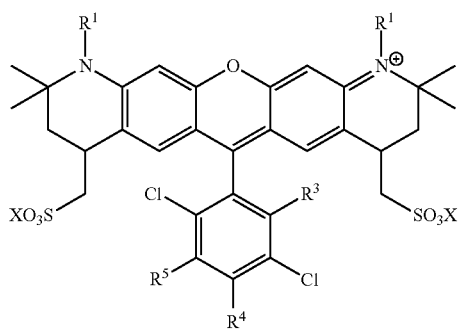

wherein:
$R^1$ and $R^2$ are independently hydrogen, or $C_1$-$C_6$ alkyl;
X is H or a counterion;
$R^3$ is carboxylate;
One of $R^4$ and $R^5$ is hydrogen and the other is Cl or $R_x$, where $R_x$ is a reactive group.

9. The compound according to claim 8, wherein $R^1$ is hydrogen, or methyl.

10. A compound having the formula;

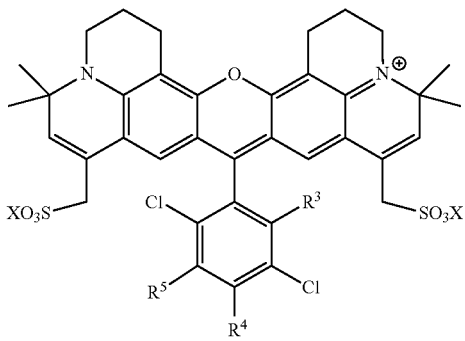

or the formula;

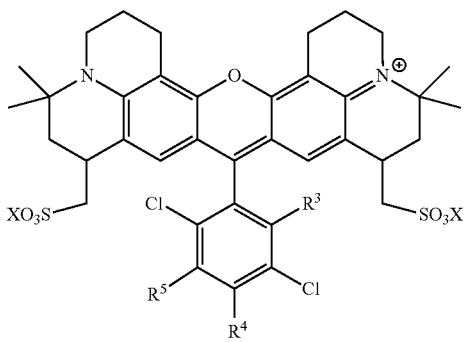

wherein:
X is H or a counterion;
$R^3$ is carboxylate or sulfonate;
$R^4$ and $R^5$ are independently hydrogen, Cl, or $R_x$, where $R_x$ is a reactive group.

11. The compound according to claim 10, wherein $R^3$ is carboxylate.

12. The compound according to claim 11, wherein one of $R^4$ and $R^5$ is hydrogen and the other $R_x$.

* * * * *